United States Patent [19]

Chiang et al.

[11] Patent Number: 6,028,150
[45] Date of Patent: Feb. 22, 2000

[54] FULLERENE-DERIVED METALLOCENE

[75] Inventors: Long Y. Chiang, Taipei; Taizoon A. Canteenwala, Hsin-Tien, both of Taiwan

[73] Assignee: Chinese Petroleum Corporation, Taipei, Taiwan

[21] Appl. No.: 09/169,681

[22] Filed: Oct. 9, 1998

Related U.S. Application Data

[62] Division of application No. 09/072,365, May 4, 1998.
[51] Int. Cl.$^7$ ................ C08F 4/64; C07F 17/00
[52] U.S. Cl. ............ 526/127; 526/160; 526/351; 526/943; 502/103; 502/117; 556/43; 556/53; 556/58; 556/136; 556/143
[58] Field of Search .................. 556/43, 53, 58, 556/136, 143; 526/127, 160, 943, 351; 502/103, 117

[56] References Cited

PUBLICATIONS

Ballenweg et al., J. Chem. Soc., Chem. Commun., pp. 2269–2270, 1994.
Ballenweg et al., Tetrahedron Letters, Vo. 34, No. 23, pp. 3737–3740, 1993.

*Primary Examiner*—Porfirio Nazario-Gonzalez
*Attorney, Agent, or Firm*—Harness, Dickey & Pierce, P.L.C.

[57] ABSTRACT

The present invention relates to a novel fullerene-derived metallocene. Such fullerene-derived metallocene can be used as the catalyst for preparing olefin polymers.

6 Claims, No Drawings

FULLERENE-DERIVED METALLOCENE

This is a division of U.S. patent application Ser. No. 09/072,365, filed May 4, 1998, now allowed.

BACKGROUND OF THE INVENTION

1. Field of the Invention:

The present invention relates to a fullerene-derived metallocene, and more particularly to a fullerene-derived metallocene suitable for use as a catalyst for preparing olefin polymers.

2. Description of the Prior Art:

Polyolefins have been synthesized by Ziegler-Natta catalysts for over three decades. This chemistry has evolved into a major industrial process which involves an intensive catalytic coordination chemistry of transition metal complexes. Enormous variations of transition metal-derived catalyst systems have thus been developed for these purposes. The ongoing trend of producing new polyolefins requires a better control of the molecular structure and molecular weight of resulting polyolefins.

Over the past few years, increasing amounts of research on the utility of metallocene catalysts in the polymerization of olefins, especially α-olefins, have progressively replaced the development of Ziegler-Natta-related chemistry. Advantages of the metallocene catalyst application include the versatility of these catalysts in regulating the tacticity of the polymer formed and the increased activity of these catalysts towards higher α-olefins as compared with traditional Ziegler-Natta catalysts.

Fullerenes are a class of carbon molecule having an even number of carbon atoms arranged in the form of a closed hollow cage, typically spheroid, wherein the carbon-carbon bonds define a polyhedral structure.

Several functionalized fullerene derivatives have been reported. For example, fullerenes with relatively small functional groups or addends such as amido, alkoxy, and halides have been described. See, e.g., U.S. Pat. No. 5,177,248; European Application No. 546,718 (treatment of unfunctionalized fullerenes with trifluoromethanesulfonic acid and nucleophiles to form alkoxylated fullerenes); European Application No. 575,129 (treatment of unfunctionalized fullerenes with sulfuric acid to form sulfated fullerenes). Macromolecules have also been reported to attach fullerenes. For example, U.S. Pat. No. 5,635,581 discloses a fullerene polymer which includes a fullerene core and a plurality of prepolymer units.

However, until now, no one has ever disclosed attaching metallocenes to a fullerene core.

SUMMARY OF THE INVENTION

Therefore, the object of the present invention is to provide a fullerene-derived metallocene.

To achieve the above-mentioned object, a fullerene-derived metallocene is developed in the present invention, which is represented by the formula of

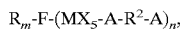

wherein F is a fullerene core,

R is independently selected from the group consisting of H, O, $C_{1-20}$ linear and branched alkyl, $C_{6-40}$ aryl, $C_{7-40}$ alkylaryl, and $C_{7-40}$ arylalkyl, M is a transition metal, X is independently a halogen, hydride, alkyl, aryl or chelating group, A is independently unsubstituted and substituted cyclopentadienyl, unsubstituted and substituted indenyl, unsubstituted and substituted fluorenyl, a fused ring containing cyclopentadienyl, indenyl, or fluorenyl moiety, $R^2$ is a $C_{1-6}$ linear, branched or cyclic alkylene group, an alkyl substituted silanylene group or an alkyl substituted silaalkylene group, which is bridged between the two A groups, p and q are positive integers, and the sum of 1+p+q is equal to the oxidation state of M, t is a positive integer, and the sum of 3+t is equal to the oxidation state of M, m is an integer from 1 to 10, and n is an integer from 1 to 10.

In the polymerization mechanism, the electronic state of the transition metal center of a metallocene catalyst may play a major role in determining the reaction activity with olefins at all three intermediate states. Once the fullerene core is attached to the transition metal of a metallocene, the electronic state of the transition metal center will be altered, leading to a profound change in the polymerization activities toward olefins.

Aside from the electronic effect of fullerenic molecular orbitals on the metal center of metallocene catalysts, the unique ball-shape structure of the $C_{60}$ cage provides an unequivocal physical barrier around the catalytic metal center in the obtained fullerene-derived metallocene. The enhanced steric hindrance at the α-olefin polymerization site should regulate more effectively the stereochemistry of polyolefins leading to isotactic polymers or stereo-block polymers.

Thus, in comparison with the conventional metallocene catalyst, when the fullerene-derived metallocene of the present invention is used as a catalyst for preparing olefin polymers, regulation of the polymer tacticity can be achieved partly by the variation of the electronic and steric structure of the ligand, i.e. fullerene, attached on the transition metal.

As will be described in more detail below, methods of preparing such fullerene-derived metallocenes and methods of preparing olefin polymers using such fullerene-derived metallocene as the catalyst are also within the invention.

DETAILED DESCRIPTION OF THE INVENTION

The present invention is the first time that metallocenes have been attached onto a fullerene core. The fullerene-derived metallocene thus obtained is represented by the formula of

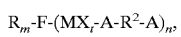

wherein F is a fullerene core,

R is independently selected from the group consisting of H, O, $C_{1-20}$ linear and branched alkyl, $C_{6-40}$ aryl, $C_{7-40}$ alkylaryl, and $C_{7-40}$ arylalkyl, M is a transition metal, X is independently a halogen, hydride, alkyl, aryl or chelating group, A is independently unsubstituted and substituted cyclopentadienyl, unsubstituted and substituted indenyl, unsubstituted and substituted fluorenyl, a fused ring containing cyclopentadienyl, indenyl, or fluorenyl moiety, $R^2$ is a $C_{1-6}$ linear, branched or cyclic alkylene group, an alkyl substituted silanylene group or an alkyl substituted silaalkylene group, which is bridged between the two A groups, p and q are positive integers, and the sum of 1+p+q is equal to the oxidation state of M, t is a positive integer, and the sum of 3+t is equal to the oxidation state of M, m is an integer from 1 to 10, preferably 3 to 10, and n is an integer from 1 to 10, preferably 3 to 10.

The term "fullerene core" refers to a fullerene, such as $C_{60}$, $C_{70}$, $C_{76}$, $C_{78}$, $C_{82}$, $C_{84}$, or $C_{92}$, which may be substituted with an alkyl, alkoxy, aryl or organocarboxy group with between 1 and 20 carbon atoms, and which may also be functionalized with amino, hydroxy or other groups not bonded to a prepolymer unit.

M is a Group IVB, VB, VIB, or VIII B transition metal, preferably zirconium, titanium, vanadium or hafnium.

Exemplary R groups are H, O, methyl, ethyl, propyl, butyl, amyl, isoamyl, hexyl, isobutyl, heptyl, octyl, nonyl, dicyl, cetyl, 2-ethylhexyl, phenyl, and the like.

The substituent of the substituted cyclopentadienyl, indenyl, or fluorenyl is independently selected from the group consisting of $C_{1-20}$ linear and branched alkyl, $C_{6-40}$ aryl, $C_{7-40}$ alkylaryl, and $C_{7-40}$ arylalkyl. Representative examples of A include $\eta^5$-cyclopentadienyl, $\eta^5$-methylcyclopentadienyl, $\eta^5$-tetramethylcyclopentadienyl, $\eta^5$-pentamethylcyclopentadienyl, $\eta^5$-n-butylcyclopentadienyl, indenyl, tetrahydroindenyl, fluorenyl, and octahydrofluorenyl.

Exemplary $R^2$ linear alkylene groups are methylene, ethylene, propylene, butylene, pentylene, hexylene, and the like. Exemplary $R^2$ cyclic alkylene groups are cyclobutylene, cyclopentylene, cyclohexylene and the like. Exemplary $R^2$ alkyl substituted silanylene groups are dimethylsilanylene, tetramethyldisilanylene, methylethylsilanylene, diethylsilanylene and the like.

Preferably $R^2$ is ethylene or dimethylsilanylene.

The attachment of metallocenes on a fullerene core, simply speaking, occurs when one of the ligands of the conventional metallocene is replaced by the fullerene core. Since the fullerene core is a very large cage, once the fullerene core is reacted with the metallocene, 1 to 10 metallocene molecules can be attached on a sole fullerene core, given that the molar ratio is appropriately controlled. Therefore, the fullerene-derived metallocene may be a mixture. For example, the product may include a three metallocene-attached fullerene, a four metallocene-attached fullerene, and a five metallocene-attached fullerene.

Generally speaking, there are at least two methods for preparing the fullerene-derived metallocene of the present invention.

The first method involves directly reacting a fullerene core with a metallocene, such that one of the ligands of the metallocene is replaced by the fullerene, and 1 to 10 metallocene molecules can be attached on a sole fullerene core. For example, when the metallocene $MRX_pA_q$ is reacted with a fullerene, R group is replaced by the fullerene; thus, the obtained product is $R_m$-F-$(MX_pA_q)_m$. m indicates the quantity of the metallocene attached to the fullerene, and the definitions for the other symbols are the same as previously described.

When R is H, the metallocene $MHX_pA_q$ can be prepared by reacting $MX_{p+1}A_q$ with a reducing agent. The reducing agent may be a metal hydride. Representative examples of the metal hydride include lithium aluminum hydride or superhydride. For example, bis($\eta^5$-cyclopentadienyl) zirconium dichloride is reduced by reaction with lithium aluminum hydride to obtain bis($\eta^5$-cyclopentadienyl) hydridozirconium chloride, which is then reacted with $C_{60}$ to obtain $H_m$-$C_{60}$-$[Cp_2ZrCl]_m$, a mixture of fullerene-derived metallocene compounds, via hydrozirconation reaction. It is noted that the replacement of Cl on the starting metallocene, $Cp_2ZrCl_2$, with $C_{60}$ leads to the final fullerene-derived metallocene product.

Similarly, when the metallocene $MRX_t$-A-$R^2$-A is reacted with a fullerene, R group is replaced by the fullerene; thus, the obtained product is $R_m$-F-$(MX_t$-A-$R^2$-A$)_m$. m indicates the quantity of the metallocene attached to the fullerene, and the definitions for other symbols are the same as previously described.

When R is H and t is 1, the metallocene MHX-A-$R^2$-A can be prepared by reacting MX-A-$R^2$-A with a reducing agent. For example, rac-ethylene bis(indenyl) zirconium dichloride is reduced by reaction with lithium aluminum hydride to obtain rac-ethylene bis($\eta^5$-indenyl) hydridozirconium chloride, which is then reacted with $C_{60}$ to obtain $H_m$-$C_{60}$-$[(rac\text{-}indenyl)_2ZrCl]_m$, a mixture of fullerene-derived metallocene compounds, via hydrozirconation reaction. It is noted that the replacement of Cl on the starting metallocene, (rac-indenyl)$_2$ZrCl$_2$, with $C_{60}$ leads to the final fullerene-derived metallocene product.

The second method for preparing the fullerene-derived metallocene of the present invention involves first reacting a fullerene with a reducing agent to form a polyanionic fullerene ($F^{-m}$). Then, the polyanionic fullerene is reacted with a metallocene of $MX_{p+1}A_q$ to obtain the desired product F-$(MX_pA_q)_m$ via a nucleophilic substitution reaction. m indicates the quantity of the metallocene attached to the fullerene, and the definitions for other symbols are the same as previously described. The reducing agent may be a compound containing a Group IA metal, such as lithium naphthalide, sodium naphthalide, and potassium naphthalide. For example, when a polyanionic $C_{60}$ is reacted with $CpZrCl_3$ to obtain $C_{60}(CpZrCl_2)_m$, it is noted that the replacement of Cl on $CpZrCl_3$ with $C_{60}$ leads to the final fullerene-derived metallocene product.

When the reducing agent used for reducing a fullerene is an alkyl metal having the formula $R^3$-$M^3$, the obtained polyanionic fullerene is bonded to said alkyl group ($R^3$), and a polyalkylated polyanionic fullerene $R^3_m(F^{-m})$ is obtained. $R^3$ is $C_{1-30}$ alkyl, aryl alkylaryl, or arylalkyl, $M^3$ is an alkaline metal, m is an integer from 1 to 10, and the other symbols are defined as above. Then, the polyalkylated polyanionic fullerene is reacted with a metallocene having the formula of $MX_{p+1}A_q$ to form the fullerene-derived metallocene $R^3_m$-F-$(MX_pA_q)_n$.

When the fullerene core is $C_{60}$, the alkyl metal is butyl lithium, the reaction of $C_{60}$ and butyl lithium leads to a polybutylated polyanionic $C_{60}$, which is then reacted with $CpZrCl_3$ to obtain polybutylated $C_{60}$-coordinated $CpZrCl_2$ via a nucleophilic substitution reaction. It is noted that the replacement of Cl on $CpZrCl_3$ with polybutylated $C_{60}$ leads to the final fullerene-derived metallocene product.

According to the present invention, the obtained fullerene-derived metallocene can be used as the catalyst for preparing olefin polymers. The process includes polymerizing at least one olefin with another monomer under polymerizing conditions in the presence of a catalytically effective amount of the fullerene-derived metallocene catalyst composition. The catalyst composition can be the fullerene-derived metallocene alone or the fullerene-derived metallocene combined with an activating cocatalyst.

The activating cocatalyst can be methyl aluminoxane (MAO), a trialkyl aluminum, a dialkyl aluminum, a salt of an inert and non-coordinating anion, or a mixture thereof.

The trialkyl aluminum can be selected from the group consisting of trimethyl aluminum, triethyl aluminum, tripropyl aluminum, trisopropyl aluminum, tributyl aluminum, and triisobutyl aluminum (TIBA).

The inert and non-coordinating anion can be a borate. Borates that are suitable for use in the present invention include N,N-dimethyl anilinium tetrakis(pentafluorophenyl) borate, triphenyl carbenium tetrakis(pentafluorophenyl) borate, trimethyl ammonium tetrakis(pentafluorophenyl) borate, ferrocenium tetrakis(pentafluorophenyl)borate, dimethyl ferrocenium tetrakis(pentafluorophenyl)borate, and silver tetrakis(pentafluorophenyl)borate.

Preferably, the activating cocatalyst is methyl aluminoxane, or a mixture of a trialkyl aluminum and a borate.

By using the catalyst composition of the present invention, an olefin polymer can be synthesized. At least one olefin monomer and another monomer can be subjected to polymerization under polymerizing conditions in the presence of a catalytically effective amount of the metallocene complex catalyst of the present invention.

Suitable olefin monomers can be ethylene or α-olefins. The polymers to be prepared by the process of the present invention can be homopolymers of ethylene, homopolymers of α-olefins, copolymers of α-olefins, and copolymers of ethylene and α-olefins. Examples of the α-olefins include those olefins having from 3 to 12 carbon atoms, such as propylene, 1-butene, 1-pentene, 1-hexene, 1-octene, 1,3-butadiene and 1,5-hexadiene.

Specifically, the catalyst system disclosed in the present invention can be used to prepare ethylene homopolymers, including high density polyethylene (HDPE) having broad, bimodal, or multimodal molecular weight distributions for applications such as high molecular weight films and blow molding.

Also, the catalyst system disclosed in the present invention can be used to prepare a copolymer of ethylene and propylene (EPM). Also, a copolymer of ethylene, a $C_{3-12}$ α-olefin, and a non-conjugated diene can be prepared. For example, when the $C_{3-12}$ α-olefin used is propylene, a copolymer of ethylene, propylene, and a non-conjugated diene can be prepared, which is referred to as EPDM. The suitable non-conjugated diene can be 5-ethylidene-2-norbornene (ENB), 5-methylene-2-norbornene, 5-vinylidene-2-norbornene, 1,4-hexadiene (HD), or dicyclopentadiene (DCPD).

The novel catalyst system disclosed in the present invention can be used in slurry reaction conditions, gas phase, and solution polymerization reaction conditions. Polymerization is typically carried out at a temperature of 0° to 250° C., and at an atmospheric pressure to 3,000 psi.

The following examples are intended to illustrate the process and the advantages of the present invention more fully without limiting its scope, since numerous modifications and variations will be apparent to those skilled in the art.

EXAMPLES 1

Synthesis of $C_{60}$ Coordinated Biscyclopentadienyl Zirconium Chloride-1

Hydrozirconation reaction of fullerenes was carried out with a suspended Schwartz's reagent ($CP_2ZrHCl$) in a toluene solution of $C_{60}$ analogous fullerenes, containing a molar ratio of $C_{60}:Cp_2ZrHCl$ of 1:1. While the reaction mixture was stirred at ambient temperatures for 24 h, a color change of the medium from brown to reddish brown was observed, along with the disappearance of suspended $Cp_2ZrHCl$ particles. After removal of toluene under vacuum, the resulting brown solids were extracted by methylene chloride and dried. Since the $C_{60}$ molecule itself is insoluble and $Cp_2ZrHCl$ is barely soluble in methylene chloride, the $CH_2Cl_2$-soluble fraction of brown solids (38% yield) was indicative of reaction products other than both starting materials.

The infrared spectrum of this fraction showed two bands centered at 807 and 745 $cm^{-1}$, corresponding to absorptions of cyclopentadienyl functions, and the disappearance of a Zr—H infrared absorption band centered at 1420 $cm^{-1}$. The $^1H$ NMR spectrum of the methylene chloride-soluble fraction displayed a singlet peak at δ 6.31, indicating retention of the bis($\eta^5$-cyclopentadienyl) zirconium moiety in the product. The $CH_2Cl_2$-insoluble residues were further washed with THF to reveal sharp infrared absorptions in close resemblance to those of unreacted $C_{60}$ molecules at 1428, 1180, 577, and 526 $cm^{-1}$.

EXAMPLES 2

Synthesis of $C_{60}$ Coordinated Biscyclopentadienyl Zirconium Chloride-2

To minimize the unreacted $C_{60}$ molecules obtained in Example 1, a higher molar quantity of Schwartz's reagent was used. In this case, the hydrozirconation reaction of fullerenes was carried out with a suspended Schwartz's reagent in a toluene solution of $C_{60}$, containing a molar ratio of $C_{60}:Cp_2ZrHCl$ of 1:2. Under similar reaction conditions and workup procedures as described in Example 1, the resulting reaction products were isolated into three solubility fractions: the methylene chloride-soluble fraction, the THF-soluble fraction, and insoluble residues.

The infrared spectrum of the methylene chloride-soluble fraction showed two bands centered at 806 and 749 $cm^{-1}$, corresponding to absorptions of cyclopentadienyl functions, and the disappearance of a Zr—H infrared absorption band centered at 1420 $cm^{-1}$. The $^1H$ NMR spectrum of this fraction also showed the chemical shift of $\eta^5$-cyclopentadienyl protons at δ 6.31 as a singlet peak. The amount of insoluble residues was found to be less than that in Example 1 and the amount of THF-solubles was in a trace quantity.

EXAMPLE 3

Synthesis of $C_{60}$ Coordinated Biscyclopentadienyl Zirconium Chloride-3

In addition to Examples 1 and 2, two other hydrozirconation reactions of fullerenes were carried out with a suspended Schwartz's reagent in a toluene solution of $C_{60}$ in a molar ratio of $C_{60}:Cp_2ZrHCl$ of 2:1 and 1:0.75, respectively. Reaction conditions similar to those described in Examples 1 and 2 were applied. Modified workup procedures were used to incorporate toluene washings on the $CH_2Cl_2$-insoluble solids instead of THF. Results confirmed that the solids were highly extractable with toluene consistent with the moderate solubility of $C_{60}$ in toluene. In both experiments, a nearly 75% yield of $C_{60}$ was recovered, as expected, along with a roughly 20% yield of the methylene chloride-soluble materials.

EXAMPLE 4

Synthesis of $C_{60}$ Coordinated Biscyclopentadienyl Zirconium Chloride-4

The Schwartz's reagent is relatively reactive toward moisture and air, which reduces its shelf-life significantly. To ensure its purity content prior to use for the reaction, a repurification procedure is often followed. However, it is rather difficult to identify the actual purity level of commercially available Schwartz's reagent even after purification. We thus undertook the preparation of bis($\eta^5$-cyclopentadienyl) hydridozirconium chloride by a reduction reaction of bis($\eta^5$-cyclopentadienyl) zirconium dichloride in dry THF with lithium aluminum hydride in diethyl ether to afford a mixture of hydridozirconium products as white precipitates in 85% yield, as shown below. Bis($\eta^5$-cyclopentadienyl) dihydridozirconium compound can be converted to the desired product, $Cp_2ZrHCl$, by washing under stirring with methylene chloride. The resulting products were isolated and characterized by the $^1H$ NMR spectroscopic measurement showing a singlet cyclopentadienyl proton at $\delta$ 6.31.

The freshly prepared bis($\eta^5$-cyclopentadienyl) hydridozirconium chloride was used directly in the hydrozirconation reactions of fullerenes. Similar reaction conditions as those of Example 1 were carried out with suspended $Cp_2ZrHCl$ in a toluene solution of $C_{60}$ with a molar ratio of $C_{60}$ to $Cp_2ZrHCl$ of 1:2. After a reaction period of 24 h, the resulting toluene-insoluble solids were separated from the reaction solution by a centrifuge technique. The clear dark-brown supernatant liquid was dried under vacuum to afford dark brown solids, which were extracted repeatedly with methylene chloride to give an improved yield of brown solids as compared with those obtained from previous examples.

EXAMPLE 5

Synthesis of $C_{60}$ Coordinated Biscyclopentadienyl Zirconium Chloride-5

One approach to minimize the deliberate decomposition of bis ($\eta^5$cyclopentadienyl) hydridozirconium chloride in solution is to generate the Schwartz's reagent in situ in the reaction medium. In this case, superhydride was used as a source of the hydride anion for the reduction of zirconocene dichloride. Experimentally, zirconocene dichloride, $Cp_2ZrCl_2$, in dry THF was treated with superhydride ($LiEt_3BH$, 1.0 M) to yield a dark yellow solution of $Cp_2ZrHCl$. The solution was added to a purple solution of $C_{60}$ (0.65 equiv) in toluene to give a dark brown solution, which turned slowly to reddish brown upon stirring at ambient temperatures. Disappearance of the characteristic purple color of $C_{60}$ in solution clearly indicated a reaction of $C_{60}$ with $Cp_2ZrHCl$ to yield the corresponding $C_{60}$ derivatives, which often showed a brown color in nature. At the end of reaction, the reaction mixtures were centrifuged to remove suspended, insoluble particles. The resulting supernatant was dried by solvent evaporation under vacuum to afford brown solids, which were subsequently extracted by methylene chloride to isolate the reaction products. Infrared spectra of this methylene chloride-soluble fraction of products were compared with that of the methylene chloride-soluble fraction of products obtained from Example 1, showing a good agreement of major IR absorption bands, corresponding to cyclopentadienyl functions, centered at 805 and 735 $cm^{-1}$.

EXAMPLE 6

Synthesis of $C_{60}$ Coordinated Monocyclopentadienyl Zirconium Dichloride-1

Utilization of the hydrozirconation reaction as a synthetic strategy for the preparation of fullerene-derived zirconocene complexes has been extended to include other cyclopentadienyl zirconium chlorides, such as ($\eta^5$-cyclopentadienyl) zirconium trichloride. The corresponding zirconium hydride derivative, resembling Schwartz's reagent, can be, in principle, synthesized by the hydride reduction of cyclopentadienyl zirconium trichloride using lithium aluminum hydride as a reducing agent. The reaction results in a product of ($\eta^5$-cyclopentadienyl) hydridozirconium dichloride as shown below. Hydrozirconation reaction of the $C_{60}$ molecule with ($\eta^5$-cyclopentadienyl) hydridozirconium dichloride under a similar reaction mechanism as that of the reaction with the Schwartz's reagent may give products of dichloro-($\eta^5$-cyclopentadienyl) zirconium hydridofulleride analogous compounds. Interestingly, this type of cyclopentadienyl zirconium fulleride compound bears a close resemblance to zirconocene dichloride by replacing one cyclopentadienyl ring with a $C_{60}$ cage.

The reaction was carried out by the treatment of cyclopentadienyl zirconium trichloride, $CpZrCl_3$, dissolved in dry THF with either lithium aluminum hydride or superhydride, $LiEt_3BH$, at ambient temperatures for 1 h, to generate $CpZrHCl_2$ in situ. The resulting pale yellow solution was added directly to a $C_{60}$ solution in toluene. Upon stirring at 25° C., the characteristic purple color of the $C_{60}$ solution was observed to turn slowly into dull brown. After a reaction period of 24 h, toluene-insoluble particles of the reaction mixture were separated by a centrifuge technique. Removal of the solvent (toluene) from the supernatant under vacuum yielded brown solids as products, which were extracted repeatedly by methylene chloride to obtain the desired fraction of catalysts.

After evaporation of the solvent, the resulting brown solids were characterized by both the $^1H$ NMR spectrum showing a singlet peak at $\delta$ 6.31, and the infrared spectrum displaying two sharp bands centered at 1019 and 822 $cm^{-1}$, corresponding to IR absorptions of the cyclopentadienyl function. Comparison of the overall IR spectrum of this product with the IR absorption spectrum of $CpZrCl_3$ revealed the occurrence of an effective transformation reaction from cyclopentadienyl zirconium trichloride to the corresponding dichloro-($\eta^5$-cyclopentadienyl) zirconium hydridofulleride analogous compounds.

EXAMPLE 7

Synthesis of Rac-Ethylene Chloro-Bis(indenyl) Zirconium Hydridofulleride

Rac-ethylene bis(indenyl) zirconium dichloride is one of effective zirconium analogous metallocene catalysts known to date. Incorporation of a fullerene cage in this class of zirconium complexes presents a new approach aiming for modification of the electronic structure of the zirconium metal center, which may exhibit a profound effect on the polymerization of ethylene and $\alpha$-olefins. Synthesis of chloro-bis(indenyl) zirconium fullerides can be accomplished by the use of hydrozirconation reaction of rac-ethylene bis(indenyl) hydridozirconium chloride with the $C_{60}$ molecule.

In this experiment, rac-ethylene bis(indenyl) hydridozirconium chloride was generated in situ in the reaction medium (THF) by reacting rac-ethylene bis(indenyl) zirconium dichloride with either lithium aluminum hydride or superhydride, LiEt$_3$BH, at ambient temperatures for 1 h. The resulting bright yellow-colored solution of hydridozirconium chloride complexes was added to the C$_{60}$ solution in toluene. Upon stirring at 25° C., the characteristic purple color of the C$_{60}$ solution was observed to turn slowly into dark brown or black. After a reaction period of 24 h, toluene-insoluble particles of the reaction mixture were separated by a centrifuge technique. Removal of solvent (toluene) from the supernatant solution under vacuum yielded dark solids, which were extracted repeatedly by methylene chloride to obtain the desired fraction of catalysts.

After the evaporation of the solvent, the resulting dark brown solids were characterized by both the $^1$H NMR spectrum showing a singlet peak at δ 6.31, and the infrared spectrum displaying sharp bands centered at 768–747 cm$^{-1}$, corresponding to IR absorptions of the indenyl function. The methylene chloride-insoluble solids showed sharp fullerenic IR absorption peaks consistent with the presence of C$_{60}$ molecules and the absence of indenyl functional groups. Comparison of the overall IR spectrum of this product with the IR absorption spectrum of (rac-ind)$_2$ZrCl$_2$ revealed an effective conversion of rac-ethylene bis(indenyl) zirconium dichloride to the corresponding rac-ethylene chloro-bis (indenyl) zirconium hydridofulleride analogous compounds.

EXAMPLE 8

Synthesis of C$_{60}$ Coordinated Monocyclopentadienyl Zirconium Dichloride-2

The treatment of a fullerene (C$_{60}$ and C$_{70}$) solution in toluene with sodium naphthalide led to the formation of a black reaction mixture, which was added to a solution of ($\eta^5$-cyclopentadienyl) zirconium trichloride, CpZrCl$_3$, in dimethoxyethane (DME). Upon addition of CpZrCl$_3$, the reaction solution was observed to turn brown slowly. The workup procedures involved evaporation of the solvent and the washing of the resulting brown solids with hexane for the removal of naphthalene, which was identified by its $^1$H NMR spectrum. The hexane-insoluble products were extracted with methylene chloride to afford the methylene chloride-soluble fraction and the insoluble fraction, which was further extracted by THF. The solvent of all brown soluble fractions was removed under vacuum.

The infrared spectrum of both the methylene chloride-soluble fraction and the ethylacetate-soluble fraction showed absorption bands centered at 1020 and 828 cm$^{-1}$, indicating the presence of cyclopentadienyl groups in both fractions. $^1$H NMR spectrum of both the methylene chloride-soluble fraction and the ethylacetate-soluble fraction showed a cluster of proton peaks centered in the region of δ 6.2–6.6, corresponding to cyclopentadienyl protons. The THF-soluble fraction did not contain any cyclopentadienyl functions, as the corresponding proton peaks were absent in its $^1$H NMR spectrum.

EXAMPLE 9

Synthesis of C$_{60}$ Coordinated Monocyclopentadienyl Zirconium Dichloride-3

In other separate reaction attempts under similar reaction conditions, the hexaanionic C$_{60}$ intermediate was allowed to react with ($\eta^5$-cyclopentadienyl) zirconium trichloride (9.0 equiv) in dimethoxyethane (DME) for a longer reaction period (12 h) at room temperature. The resulting reaction mixtures were subjected to a similar workup procedure via solvent removal in vacuum and product fractionation by a solvent extraction technique into fractions of methylene chloride solubles, ethylacetate solubles, tetrahydrofuran solubles, and methylene chloride-insoluble solids.

Nearly identical results were achieved in terms of the product yield and the spectroscopic data for each fraction compared to those of fractions isolated from the previous reaction under a shorter reaction time, said results showing characteristic infrared bands corresponding to absorptions of the cyclopentadienyl ring at 1442, 1020, and 828 cm$^{-1}$ in the infrared spectra of the methylene chloride soluble and ethylacetate soluble fractions. This data indicated an increase of solvent solubility of the C$_{60}$ molecule being functionalized with an increased number of Cp-containing metal centers. Among soluble fractions of materials, the methylene chloride soluble fraction was the major product with a 60–80% yield of total solubles, the ethylacetate soluble fraction being the second major product with a 15–20% yield of total solubles. The compound CpZrCl$_3$ exhibited a much higher chemical reactivity toward hydrolysis with H$_2$O than that of Cp$_2$ZrCl$_2$. Therefore, most of the unconverted CpZrCl$_3$ in the reaction mixture was decomposed into insoluble solids containing several hydrolyzed clusters, which gave four broad infrared bands centered at 3420 (—OH), 1660, 1050, and 480 cm$^{-1}$ corresponding to absorptions of the zirconium oxide (Zr—O) functional groups. In cases of the methylene chloride soluble fraction and the ethylacetate soluble fraction, two prominent singlet proton peaks at δ 6.39 and 6.38, respectively, were detected. Chemical shift of this proton peak is closely related to that of cyclopentadienyl protons in ($\eta^5$-cyclopentadienyl) zirconium trichloride, CpZrCl$_3$, and bis ($\eta^5$-cyclopentadienyl) zirconium dichloride, Cp$_2$ZrCl$_2$, at δ 6.40 (in CDCl$_3$-DMSO-d$_6$) or 6.55 (in acetone-d$_6$) and 6.49 (in CDCl$_3$), respectively. Since the fullerene molecules exhibit limited solubility in methylene chloride along with the lack of characteristic C$_{60}$ absorption bands in the infrared spectrum, the dark brown color of methylene chloride solubles indicated the existence of functionalized C$_{60}$ cages in this fraction. Thus, both IR and NMR spectra support the proposed chemical structure of main components in the methylene chloride soluble fraction being the C$_{60}$-coordinated ($\eta^5$-cyclopentadienyl) zirconium dichloride derivatives.

EXAMPLE 10

Synthesis of C$_{60}$ Coordinated Monocyclopentadienyl Zirconium Dichloride-4

By studying the stability of sodium naphthalide in DME, it was noted that good control of the equivalent addition of sodium naphthalide can be achieved by using a diluted solution or a low concentration of the sodium naphthalide stock solution. Since decomposition of sodium naphthalide with a trace quantity of moisture and oxygen is possible, change of the solute concentration can be minimized if further addition of an amount of solvent is prevented. Persistence of a green color in the sodium naphthalide solution is indicative of its full dryness. In this case, even after following a stringent drying procedure, a certain quantity of sodium naphthalide was required to consume the reactive impurities in toluene prior to observe the appearance of the solution as green. Therefore, in this experiment, the solution of sodium naphthalide was diluted and its concentration determined by a titration method with succinic acid in DME prior to use.

A fullerene ($C_{60}$ and $C_{70}$) solution in toluene was treated with sodium naphthalide to give a black mixture, which was then added a solution of ($\eta^5$-cyclopentadienyl) zirconium trichloride, $CpZrCl_3$, in DME. Upon the addition of $CpZrCl_3$, the reaction solution was observed to turn brown slowly. The workup procedure involved evaporation of the solvent and washing of the resulting brown solids with hexane for the removal of naphthalene, which was identified by its $^1H$ NMR spectrum. The hexane-insoluble products were extracted with methylene chloride to afford the methylene chloride-soluble fraction and the insoluble fraction, which was further extracted by THF. The solvent of all brown soluble fractions was removed under vacuum. The infrared spectrum of both the methylene chloride-soluble fraction and the ethylacetate-soluble fraction showed absorption bands centered at 1020 and 828 $cm^{-1}$, indicating the presence of cyclopentadienyl groups in both fractions. The $^1H$ NMR spectrum of both the methylene chloride-soluble fraction, the ethylacetate-soluble fraction, and the THF-soluble fraction showed a cluster of proton peaks centered in a broad region of $\delta$ 6.3–6.9, corresponding to the chemical shift of cyclopentadienyl protons. Broad distribution of the chemical shift of cyclopentadienyl protons was indicative of a number of zirconocene complexes containing cyclopentadienyl functions under a different environment.

In addition, the preparation of the $C_{60}$ coordinated ($\eta^5$-cyclopentadienyl) zirconium dichloride derivatives by nucleophilic substitution methods using hexaanionic fullerenes as the key reaction intermediates was reproduced in many experiments, aiming to improve the reaction yield. It was found that the splitting pattern of aromatic Cp proton peaks of the methylene chloride-soluble fraction varied from batch to batch, presumably depending upon the quantity of the moisture content in the solvent used. For example, a singlet peak at $\delta$ 6.49 (in $CDCl_3$) was detected in the $^1H$ NMR spectrum of one methylene chloride soluble product synthesized under similar experimental conditions. Upon the addition of $DMSO-d_6$ to the same sample, the singlet peak was observed to split into two singlets at $\delta$ 6.41 and 6.49, indicating a slight upfield chemical shift of the Cp protons by 0.08 ppm induced by partial hydrolysis of the sample. Two other $^1H$ NMR spectra of the methylene chloride-soluble products isolated from separate experiments using a mixture of $CDCl_3$ and DMSO-d6 as co-solvents, showed a more complicated pattern of the Cp proton peaks ranging from $\delta$ 6.3–6.7.

EXAMPLE 11

Synthesis of $C_{60}$ Coordinated Biscyclopentadienyl Zirconium Chloride-6

A similar nucleophilic substitution reaction of the hexaanionic $C_{60}$ at the metal center of a Zr—Cl bond was extended for bis($\eta^5$-cyclopentadienyl) zirconium dichloride molecules under similar reaction conditions. In this case, $C_{60}$ molecules, dissolved in toluene, were treated with a DME solution containing sodium naphthalide (6.0 equiv) at ambient temperatures for a period of 1 h. The reaction mixture was subsequently added to bis($\eta^5$-cyclopentadienyl) zirconium dichloride ($Cp_2ZrCl_2$, 9.0 equiv) in DME and stirred at room temperature for an additional 12 h.

At the end of the reaction, solvents in the reaction medium were removed in vacuum and the resulting semi-solid products were fractionated by the solvent extraction technique into hexane solubles, methylene chloride solubles, ethylacetate solubles, tetrahydrofuran solubles, and insoluble solids. The methylene chloride soluble fraction was found to be the major product of reaction (80% yield), which showed the characteristic pronounced infrared bands corresponding to absorptions of the cyclopentadienyl ring at 1440, 1014, 806(s), and 740(s) $cm^{-1}$ in its infrared spectrum. This spectrum bears close resemblance to that of biscyclopentadienyl zirconium dichloride, $Cp_2ZrCl_2$, with absorption bands centered at 3102, 1439, 1916, 852, and 814(s) $cm^{-1}$. The $^1H$ NMR spectrum of the dark brown methylene chloride soluble fraction gave a group of peaks with one peak in the highest intensity at $\delta$ 6.31, corresponding to the chemical shift of protons in the Cp ring. The chemical shift of this peak presents a 0.18 ppm upfield shift as compared with that of the Cp protons in $Cp_2ZrCl_2$, at $\delta$ 6.49, indicating the replacement of chlorine atoms in the structure of $Cp_2ZrCl_2$ by anionic $C_{60}$ species consistent with the proposed chemical structure of $C_{60}$-coordinated biscyclopentadienyl zirconium chloride derivatives. The $^1H$ NMR spectrum of methylene chloride soluble products showed a sharp peak of cyclopentadienyl protons at $\delta$ 6.31 of a 0.2 ppm shift from that of bis($\eta^5$-cyclopentadienyl) zirconium dichloride at $\delta$ 6.50.

EXAMPLE 12

Synthesis of $C_{60}$ Coordinated Monocyclopentadienyl Zirconium Dichloride-5

Fullerene molecules dissolved in benzene were treated with n-butyl lithium in hexane (6.0 equiv) at ambient temperatures for a period of 1 h. The dark black reaction mixture was subsequently added to $CpZrCl_3$ (9.0 equiv) in DME or THF and stirred at room temperature for an additional 12 h. At the end of the reaction, solvents in the reaction medium were removed in vacuum and the resulting semi-solid products were fractionated by the solvent extraction technique into methylene chloride solubles, ethylacetate solubles, tetrahydrofuran solubles, and insoluble solids. Among them, the methylene chloride-soluble fraction was found to be among the major products (>60% yield), containing the characteristic pronounced infrared bands corresponding to absorptions of the cyclopentadienyl ring at 1441, 1019, and 828 $cm^{-1}$ in addition to infrared bands centered at 2954(s), 2926(s), and 2856 $cm^{-1}$ corresponding to absorptions of the C—H functions in n-butyl groups. The $^1H$ NMR spectrum of this fraction showed a singlet peak at $\delta$ 6.49 and two broad peaks centered at $\delta$ 0.94 and 1.57, corresponding to the characteristic chemical shift of the cyclopentadienyl protons and n-butyl protons, respectively. Both spectroscopic data were consistent with the proposed structure of poly(n-butylated) $C_{60}$-coordinated monocyclopentadienyl zirconium dichloride products.

EXAMPLE 13

Synthesis of $C_{60}$ Coordinated Monocyclopentadienyl Zirconium Dichloride-6

In a separate reaction, t-butyl lithium was used instead of n-butyl lithium under similar reaction conditions. The hexabutylated hexaanionic $C_{60}$ intermediate was allowed to react with $CpZrCl_3$ (9.0 equiv) in DME for a period of 12 h at room temperature. The resulting reaction mixture was subjected to a similar workup procedure via solvent removal in vacuum and product fractionation by the solvent extraction technique. The methylene chloride soluble fraction was found to be the major product (>75% yield) containing the characteristic pronounced infrared bands corresponding to absorptions of the cyclopentadienyl ring at 1460, 1019, and 813 $cm^{-1}$ in addition to infrared bands centered at 2959(s), 2920(s), and 2861 cm$^{-1}$ corresponding to absorptions of the C—H functions in t-butyl groups. Infrared absorptions of the cyclopentadienyl ring attached on the $C_{60}$ cage were compared with those of $CpZrCl_3$ at 1440, 1019, and 834(s) cm$^{-1}$. The $^1$H NMR spectrum of this fraction showed a singlet peak at δ 6.49 and a broad peak centered at δ 1.30, corresponding to the characteristic chemical shift of the cyclopentadienyl protons and t-butyl protons, respectively. Chemical shift of the proton peak at δ 6.49 is closely related to that of cyclopentadienyl protons in monocyclopentadienyl zirconium trichloride, $CpZrCl_3$, and in biscyclopentadienyl zirconium dichloride, $Cp_2ZrCl_2$, at δ 6.40 (in $CDCl_3$-DMSO-$d_6$) or 6.55 (in acetone-$d_6$) and 6.49 (in $CDCl_3$), respectively. Since the fullerene molecules exhibited limited solubility in methylene chloride along with the lack of characteristic $C_{60}$ absorption bands in the infrared spectrum, the dark brown color of the methylene chloride solubles indicated the existence of functionalized $C_{60}$ cages in this fraction. Thus, both IR and NMR spectra supported the proposed chemical structure of the main components of the methylene chloride soluble fraction as poly(t-butylated) $C_{60}$-coordinated monocyclopentadienyl zirconium dichloride derivatives.

EXAMPLE 14

Synthesis of $C_{60}$ Coordinated Monocyclopentadienyl Zirconium Dichloride-7

Solubility of the polyanionic fullerene is generally higher in THF than in toluene. To ensure complete dissolvation of the polyanionic fullerene in the reaction medium, the use of THF as a reaction medium is desirable. Thus, in this experiment, fullerene molecules were suspended in THF and treated with n-butyl lithium in hexane (6.0 equiv) at ambient temperatures for a period of 1 h. The dark black reaction solution was subsequently added to $CpZrCl_3$ (9.0 equiv) in DME or THF and stirred at room temperature for an additional 12 h. At the end of the reaction, solvents in the reaction medium were removed in vacuum and the resulting semi-solid products were fractionated by a solvent extraction technique into the toluene-soluble fraction, the methylene chloride-soluble fraction, and insoluble solids. Among them, the methylene chloride-soluble fraction was found to be the major product (>70% yield) containing the characteristic pronounced infrared bands corresponding to absorptions of the cyclopentadienyl ring at 1441, 1020, and 832 cm$^{-1}$, in addition to infrared bands centered at 2933, 2926, and 2856 cm$^{-1}$ corresponding to absorptions of the C—H functions in n-butyl groups.

EXAMPLE 15

Synthesis of $C_{60}$ Coordinated Monocyclopentadienyl Zirconium Dichloride-8

The reaction of fullerene molecules, which were suspended in THF, with n-butyl lithium in hexane (6.0 equiv), was allowed to proceed at −78° C. for a period of 1 h. The dark black reaction solution was subsequently added to $CpZrCl_3$ (9.0 equiv) in THF at −30° C. and stirred at that temperature for a period of 30 min. Stirring was continued overnight while the temperature of the reaction medium raised slowly from −30° C. to room temperature. At the end of the reaction, solvents in the reaction medium were removed in vacuum and the resulting semi-solid products were fractionated by a solvent extraction technique into the toluene-soluble fraction, the methylene chloride-soluble fraction, and insoluble solids. Among them, both the toluene-soluble and methylene chloride-soluble fractions were found to be the major product (>60% yield) containing the characteristic pronounced infrared bands corresponding to absorptions of the cyclopentadienyl ring at 1441, 1020, and 832 cm$^{-1}$ in addition to infrared bands centered at 2960, 2923, and 2851 cm$^{-1}$, corresponding to absorptions of the C—H functions in n-butyl groups.

EXAMPLE 16

Polymerization of propylene using $C_{60}$-coordinated monocyclopentadienyl zirconium dichloride catalysts, synthesized from hexaanionic $C_{60}$ and ($\eta^5$-cyclopentadienyl) zirconium trichloride Freshly prepared solution of sodium naphthalide in dimethoxyethane was used in the reduction reaction of fullerene ($C_{60}$ and $C_{70}$) in toluene, followed by the treatment of resulting hexaanionic $C_{60}$ with a solution of ($\eta^5$-cyclopentadienyl) zirconium trichloride, $CpZrCl_3$, in DME. The nucleophilic substitution of a chlorine atom in ($\eta^5$-cyclopentadienyl) zirconium trichloride by the hexaanionic $C_{60}$ was effective in leading to formation of $C_{60}$-coordinated monocyclopentadienyl zirconium dichloride complexes. The methylene chloride-soluble fraction of products was used as a Zr-derived catalyst in the polymerization of propylene.

In a pressure reactor (500 mL), $C_{60}$-coordinated monocyclopentadienyl zirconium dichloride complexes (10.0 mg) and toluene (50 mL) was charged in a glove box under an atmospheric pressure of nitrogen. It was then added to methylaluminoxane (MAO, 1.0 mL, 10% in heptane). Reactions between methylaluminoxane and $C_{60}$-coordinated monocyclopentadienyl zirconium dichloride complexes occurred upon standing of the mixture for 30 min. A stream of propylene gas was passed through the toluene solution, charging up the reactor to a pressure of 3.8 bar under a closed system. After the pressure reduced itself by the dissolvation of propylene into toluene, the weight increase was measured to be 1.9 g. The polymerization reaction was allowed to proceed for a period of 2 h under stirring at ambient temperatures. At the end of polymerization, ethanol (20.0 mL) was added to decompose the remaining methylaluminoxane co-catalysts. The reaction mixtures were dried under vacuum on a rotary evaporator to yield products of polypropylene (PP, 370 mg). A part of products was extracted by toluene for the GPC measurements. The GPC profiles indicated two major polypropylene fractions with the weight average molecular weight (Mw) vs the number average molecular weight (Mn) of each fraction being 80,200/79,990 and 53, 350/52,900, corresponding to a polymer polydispersity of 1.0028 for the former PP fraction and of 1.0081 for the latter PP fraction.

The infrared spectrum of the polypropylene products displayed a relatively weaker intensity of IR bands, corresponding to absorptions of hydrocarbons, as compared with those corresponding to absorptions of polar functions. Broad absorption bands centered at roughly 3440 and 600 cm$^{-1}$, corresponding to absorptions of polar functions, in both spectra may arise from the contamination of the decomposed methylaluminoxane.

EXAMPLE 17

Polymerization of propylene using $C_{60}$-coordinated monocyclopentadienyl zirconium dichloride catalysts, synthesized by butyl lithium induced nucleophilic substitution on ($\eta^5$-cyclopentadienyl) zirconium trichloride In a pressure reactor (500 mL), the corresponding poly (n-butylated) $C_{60}$-coordinated monocyclopentadienyl zirconium dichloride derivatives (10.0 mg) and toluene (50 mL)

was charged in a glove box under an atmospheric pressure of nitrogen. It was then added methylaluminoxane (MAO, 1.0 mL, 10% in heptane). Proceeding of reactions between methylaluminoxane and the corresponding poly(n-butylated) $C_{60}$-coordinated zirconium dichloride derivatives occurred upon standing of the mixture for 30 min. A stream of propylene gas was passed through the toluene solution, charging up the reactor to a pressure of 3.0 bar under a closed system. After the pressure reduced itself by the dissolvation of propylene into toluene, the weight increase was measured to be 1.5 g. The polymerization reaction was allowed to proceed for a period of 2 h under stirring at ambient temperatures. At the end of polymerization, ethanol (20.0 mL) was added to decompose the remaining methylaluminoxane co-catalysts. The reaction mixtures were dried under vacuum on a rotary evaporator to yield products of polypropylene (PP, 550 mg). A part of products was extracted by toluene for the GPC measurements. The GPC profiles indicated three major polyproplyene fractions with the weight average molecular weight (Mw) vs the number average molecular weight (Mn) of each fraction as 81,160/80,900, 52,550/52,120, and 15,150/14,790, respectively, corresponding to a polymer polydispersity of 1.0033 and 1.0078 for the former two PP fractions and of 1.025 for the latter PP fraction.

The infrared spectrum of the polypropylene products displayed a relatively weaker intensity of IR bands, corresponding to absorptions of hydrocarbons, as compared with those corresponding to absorptions of polar function. Broad absorption bands centered at roughly 3440 and 600 cm$^{-1}$, corresponding to absorptions of polar functions, in both spectra may arise from contamination of the decomposed methylaluminoxane.

The foregoing description of the preferred embodiments of this invention has been presented for purposes of illustration and description. Obvious modifications or variations are possible in light of the above teaching. The embodiments were chosen and described to provide the best illustration of the principles of this invention and its practical application to thereby enable those skilled in the art to utilize the invention in various embodiments and with various modifications as are suited to the particular use contemplated. All such modifications and variations are within the scope of the present invention as determined by the appended claims when interpreted in accordance with the breadth to which they are fairly, legally, and equitably entitled.

What is claimed is:

1. A process for preparing an olefin polymer, comprising the step of polymerizing at least one olefin with another monomer under polymerizing conditions in the presence of a catalytically effective amount of a fullerene-derived metallocene catalyst composition, wherein the fullerene-derived metallocene catalyst composition comprises a fullerene-derived metallocene represented by the formula selected from the group consisting of

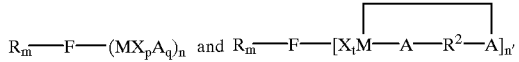

wherein F is a fullerene core,

R is independently selected from the group consisting of H, O, $C_{1-20}$ linear and branched alkyl, $C_{6-40}$ aryl, $C_{7-40}$ alkylaryl, and $C_{7-40}$ arylalkyl, M is a transition metal, X is independently a halogen, hydride, alkyl, or aryl, A is independently unsubstituted and substituted cyclopentadienyl, unsubstituted and substituted indenyl, unsubstituted and substituted fluorenyl, a fused ring containing cyclopentadienyl, indenyl, or fluorenyl moiety, $R^2$ is a $C_{1-6}$ linear, branched or cyclic alkylene group, an alkyl substituted silanylene group or an alkyl substituted silaalkylene group which is bridged between the two A groups, t is a positive integer, and the sum of 3+t is equal to the oxidation state of M, m is an integer from 1 to 10, p and q are positive integers, and the sum of 1+p+q is equal to the oxidation state of M, and n is an integer from 1 to 10.

2. The process for preparing an olefin polymer of claim 1, wherein F is selected from the group consisting of $C_{60}$, $C_{70}$, $C_{76}$, $C_{78}$, $C_{82}$, $C_{84}$, and $C_{92}$.

3. The process for preparing an olefin polymer of claim 1, wherein F is $C_{60}$.

4. The process for preparing an olefin polymer of claim 1, wherein M is a Group IVB or VB transition metal.

5. The process for preparing an olefin polymer of claim 1, wherein M is selected from the group consisting of zirconium, titanium, vanadium, and hafnium.

6. The process for preparing an olefin polymer of claim 1, wherein M is zirconium.

* * * * *